(12) United States Patent
Beachy et al.

(10) Patent No.: US 7,867,492 B2
(45) Date of Patent: Jan. 11, 2011

(54) COMPOUNDS FOR HEDGEHOG PATHWAY BLOCKADE IN PROLIFERATIVE DISORDERS, INCLUDING HEMATOPOIETIC MALIGNANCIES

(75) Inventors: Philip Arden Beachy, Stanford, CA (US); Jynho Kim, Palo Alto, CA (US)

(73) Assignees: The John Hopkins University, Baltimore, MD (US); The Board Trustees of the Leland Stanford Junior University, Palo Alto, CA (US)

(*) Notice: Subject to any disclaimer, the term of this patent is extended or adjusted under 35 U.S.C. 154(b) by 81 days.

(21) Appl. No.: 12/249,860

(22) Filed: Oct. 10, 2008

(65) Prior Publication Data
US 2009/0130091 A1 May 21, 2009

Related U.S. Application Data

(60) Provisional application No. 60/998,657, filed on Oct. 12, 2007.

(51) Int. Cl.
*A61K 38/00* (2006.01)

(52) U.S. Cl. .................................. 424/130.1; 514/504

(58) Field of Classification Search .................. None
See application file for complete search history.

(56) References Cited

U.S. PATENT DOCUMENTS

2004/0005317 A1 1/2004 Dedera et al.
2008/0287420 A1* 11/2008 Castro et al. ........... 514/212.02

OTHER PUBLICATIONS

Dierks et al Nature Medicine vol. 13 p. 944 (Aug. 2007).*
Mihich & Sellers, "Seventeenth Annual Pezcoller Symposium: Molecular Understanding of Solid Tumors", *Cancer Res.*, 65(24):11251-11254 (2005).

* cited by examiner

*Primary Examiner*—Sheela J Huff
(74) *Attorney, Agent, or Firm*—DLA Piper LLP (US)

(57) ABSTRACT

Elevated Hedgehog (Hh) pathway activity, including ligand stimulated Hh pathway activity, was detected in hematopoietic malignancy cells, and determined to be associated with growth and proliferation of the malignancy cells. Accordingly, methods are provided for treating a hematopoietic cell malignancy associated with elevated Hh pathway activity by reducing or inhibiting the Hh pathway activity. Also provided are methods of determining the responsiveness of a hematopoietic cell malignancy to treatment with an Hh pathway antagonist.

26 Claims, 8 Drawing Sheets

COMPOUNDS FOR HEDGEHOG PATHWAY BLOCKADE IN PROLIFERATIVE DISORDERS, INCLUDING HEMATOPOIETIC MALIGNANCIES

CROSS REFERENCE TO RELATED APPLICATION(S)

This application claims the benefit of priority under 35 U.S.C. §119(e) of U.S. Ser. No. 60/998,657, filed Oct. 12, 2007, the entire content of which is incorporated herein by reference.

BACKGROUND OF THE INVENTION

1. Field of the Invention

The present invention relates generally to the use of compounds to treat a variety of disorders, diseases and pathologic conditions and more specifically to the use of Hedgehog antagonists for inhibiting hedgehog pathway activity in hematopoietic cell cancer.

2. Background Information

Pattern formation is the activity by which embryonic cells form ordered spatial arrangements of differentiated tissues. Speculation on the mechanisms underlying these patterning effects usually centers on the secretion of a signaling molecule that elicits an appropriate response from the tissues being patterned. More recent work aimed at the identification of such signaling molecules implicates secreted proteins encoded by individual members of a small number of gene families.

Members of the Hedgehog family of signaling molecules mediate many important short- and long-range patterning processes during invertebrate and vertebrate development. Exemplary hedgehog genes and proteins are described in PCT publications WO 95/18856 and WO 96/17924. The vertebrate family of hedgehog genes includes at least four members, three of which, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggiewinkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh is primarily involved in morphogenic and neuroinductive activities. Given the critical inductive roles of hedgehog polypeptides in the development and maintenance of vertebrate organs, the identification of hedgehog interacting proteins and their role in the regulation of gene families known to be involved in cell signaling and intercellular communication provides a possible mechanism of tumor suppression.

Hematopoietic malignancies are frequently associated with chromosomal translocations, inversions and deletions. These genetic events may lead to the aberrant expression/activation of a proto-oncogene, to the generation of an oncogenic fusion gene, or to the deletion/inactivation of a tumor suppressor gene. Mutations of oncogenes and tumor suppressor genes have also been implicated in tumorigenesis of the hematopoietic tissue.

Evidence for a critical role of continuous Hh pathway activity in cancer growth comes from the ability of cyclopamine, a potent antagonist of the Hedgehog (Hh) signaling pathway, to inhibit cancer growth in animal models of malignancies arising in tissues such as lung, pancreas, biliary tract, prostate, skin, and brain. Thus, for example, it was observed that complete and durable cyclopamine-induced regression of aggressive prostate cancer xenografts and inhibition of prostate cancer metastasis in athymic mice, all without obvious adverse side effects.

The role of Hh pathway activity in promoting metastatic growth suggests that pathway antagonists may offer significant therapeutic improvements in the treatment of advanced prostate cancer. The ability to modulate one or more genes that are part of the hedgehog signaling cascade thus represents a possible therapeutic approach to several clinically significant cancers. A need therefore exists for methods and compounds that inhibit signal transduction activity by modulating activation of a hedgehog, patched, or smoothened-mediated signal transduction pathway, such as the Hedgehog signaling pathway, to reverse or control aberrant growth related to hematopoietic cell cancer.

SUMMARY OF THE INVENTION

The present invention is based, in part, on the determination that Hedgehog (Hh) pathway activity is elevated in hematopoietic cell malignancy as compared to corresponding normal cells, and that agents that decrease the Hh pathway activity inhibit proliferation or metastasis of hematopoietic cell malignancy. Hh ligands that can stimulate Hh pathway activity include Sonic hedgehog (SHH), Indian hedgehog (IHH), and/or Desert hedgehog (DHH). Elevated Hh pathway activity also can be due, for example, to a mutation in a Hh ligand receptor such as Patched (PTCH), wherein PTCH in inactivated, resulting in unregulated Smoothened (SMO) activity and elevated Hh pathway activity. Accordingly, the present invention provides methods of treating hematopoietic cell malignancy characterized by elevated Hh pathway activity, as well as methods of determining whether hematopoietic cell malignancy has such activity and methods of identifying agents useful for treating such tumors. As such, methods of personalized medicine are provided, wherein agents can be selected that are particularly useful for treating a particular hematopoietic cell malignancy in a subject.

In one embodiment, the invention provides a method of treating hematopoietic cell malignancy in a subject. The method includes administering to the subject at least one Hh pathway antagonist to reduce Hh pathway activity. Exemplary hematopoietic cell malignancies include, but are not limited to leukemia, such as promyelocytic leukemia (PML), acute myeloid leukemia (AML), or chronic myelogenous leukemia (CML). An Hh pathway antagonist useful in a method of the invention can be any antagonist that interferes with Hh pathway activity, thereby decreasing the abnormally elevated Hh pathway in the digestive tract tumor cells. As such, the Hh pathway antagonist can be a peptide, a polynucleotide, a peptidomimetic, a small organic molecule, or any other molecule. Hh pathway antagonists are exemplified by arsenical agents such as, arsenic trioxide (ATO) or $NaAsO_2$.

In one embodiment, the invention relates to a method of ameliorating a hematopoietic cell malignancy in a subject. The method includes administering to the subject an Hh pathway antagonist, thereby ameliorating the hematopoietic cell cancer in the subject.

The present invention further relates to a method of identifying a hematopoietic cell malignancy amenable to treatment with a Hh pathway antagonist. As such, the method provides a means to determine whether a subject having a hematopoietic cell malignancy is likely to be responsive to treatment with an Hh pathway antagonist. The method can be performed, for example, by detecting abnormally elevated Hh pathway activity in a sample of the hematopoietic malignancy cells of the subject as compared to corresponding normal cells, wherein detection of an abnormally elevated level indicates that the subject can benefit from treatment with an Hh pathway antagonist. The sample of cells can be any sample, including, for example, a tissue or bodily fluid obtained from the subject. The Hh pathway activity can be abnormally elevated due, for example, to a mutation of a gene encoding an Hh pathway polypeptide (e.g., an inactivating mutation of PTCH), or can be abnormally elevated ligand stimulated Hh pathway activity.

In one embodiment, the method of identifying a hematopoietic cell malignancy amenable to treatment with a Hh pathway antagonist includes detecting an abnormal level of expression of one or more Hh pathway polypeptide(s), including, for example, one or more Hh ligands (e.g., SHH, IHH, and/or desert hedgehog), Hh ligand receptors (e.g., PTCH), or transcription factors (e.g., a GLI family member). In one aspect, the abnormal expression is an abnormally elevated expression of one or more Hh pathway polypeptide(s), including, for example, one or more Hh ligands (e.g., SHH, IHH, and/or desert hedgehog), Hh ligand receptors (e.g., PTCH), or transcription factors (e.g., a GLI family member), or a combination of such Hh pathway polypeptides. In another aspect of this embodiment, the abnormal level of expression is an abnormally low expression of one or more Hh pathway polypeptide(s), including, for example, GLi1, which acts as a transcriptional repressor in the Hh pathway. Increased or decreased expression of an Hh pathway polypeptide can be detected by measuring the level of a polynucleotide encoding the Hh pathway polypeptide using, for example, a hybridization assay, a primer extension assay, or a polymerase chain reaction assay (e.g., measuring the level of PTCH mRNA expression and/or GLI mRNA expression); or by measuring the level the Hh pathway polypeptide(s) using, for example, an immunoassay or receptor binding assay.

In another embodiment, the method of identifying a hematopoietic cell malignancy amenable to treatment with a Hh pathway antagonist includes detecting an abnormally elevated activity of one or more Hh pathway polypeptide(s). For example, abnormally elevated activity of Hh pathway transcription factor (e.g., a GLI family member) can be detected by measuring increased binding activity of the transcription factor to a cognate transcription factor regulatory element (e.g., using an electrophoretic mobility shift assay); by measuring increased expression of a reporter gene comprising a cognate transcription factor regulatory element; or measuring expression of GLI and/or of PTCH, and/or a target of the GLI transcription factor (e.g., GLi1). In still another embodiment, the method can include detecting expression of an Hh pathway polypeptide having an inactivating mutation, wherein the mutation is associated with abnormally elevated Hh pathway activity (e.g., by detecting expression of a mutant PTCH Hh ligand receptor).

The method of identifying a hematopoietic cell malignancy amenable to treatment with a Hh pathway antagonist can further include contacting cells of the sample with at least one Hh pathway antagonist, and detecting a decrease in Hh pathway activity in the cells following contact. The decreased Hh pathway activity can be detected, for example, by measuring decreased expression of a reporter gene regulated by an Hh pathway transcription factor, or by detecting a decrease in proliferation of the hematopoietic malignancy cells. Such a method provides a means to confirm that the hematopoietic cell malignancy is amenable to treatment with an Hh pathway antagonist. Further, the method can include testing one or more different Hh pathway antagonists, either alone or in combination, thus providing a means to identify one or more Hh pathway antagonists useful for treating the particular hematopoietic cell malignancy being examined.

The sample of cells used in the present method can be cells obtained (e.g., by biopsy or other surgical procedure) from a subject having the hematopoietic cell malignancy; or can be cells that have been placed in and/or adapted to culture, including, for example, cells of an established hematopoietic malignancy cell line (or a plurality of such established cell lines, which can provide a panel for examining test agents according to the present method). Generally, though not necessarily, the method is performed by contacting the sample of cells ex vivo, for example, in a culture medium or on a solid support. As such, the methods are conveniently adaptable to a high throughput format, wherein a plurality (i.e., 2 or more) of samples of cells, which can be the same or different, are examined in parallel.

A high throughput format provides numerous advantages, including that test agents can be tested on several samples of cells from a single patient, thus allowing, for example, for the identification of a particularly effective concentration of an agent to be administered to the subject, or for the identification of a particularly effective agent to be administered to the subject. As such, a high throughput format allows for the examination of two, three, four, etc., different test agents, alone or in combination, on the cells of a subject's digestive tract tumor such that the best (most effective) agent or combination of agents can be used for a therapeutic procedure. Accordingly, in various embodiments, the high throughput method is practiced by contacting different samples of cells of different subjects with same amounts of a test agent; or contacting different samples of cells of a single subject with different amounts of a test agent; or contacting different samples of cells of two or more different subjects with same or different amounts of different test agents. Further, a high throughput format allows, for example, control samples (positive controls and or negative controls) to be run in parallel with test samples, including, for example, samples of cells known to be effectively treated with an agent being tested. Variations of the exemplified methods also are contemplated.

DETAILED DESCRIPTION OF THE INVENTION

Figure 1:
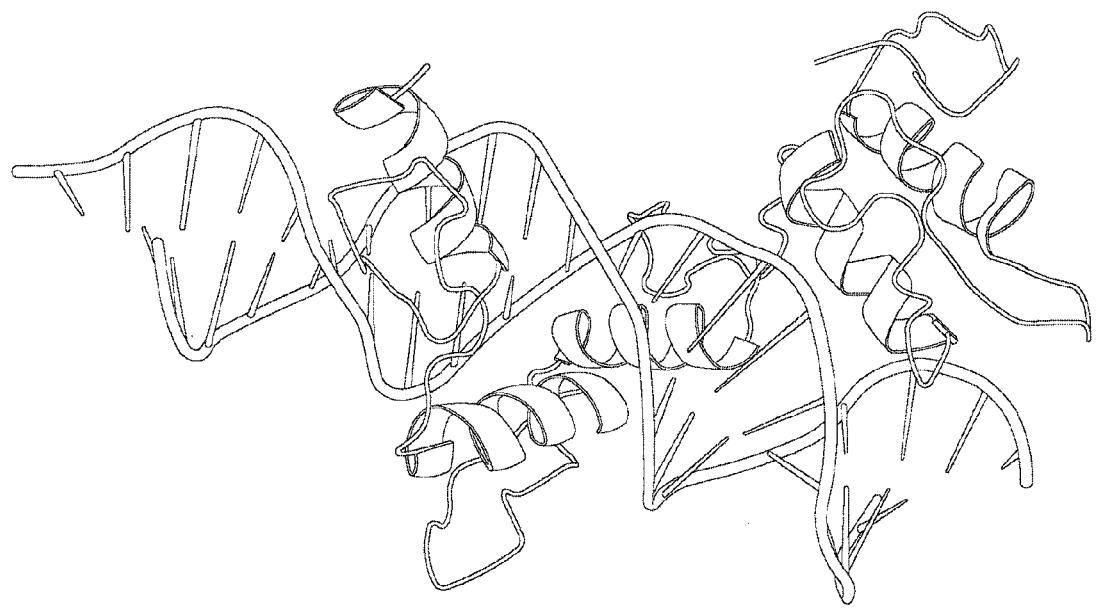
FIG. 1 is a pictorial diagram showing the structure of a Gli and DNA complex revealed by X-ray crystallography.

The present invention is based on the identification of elevated hedgehog (Hh) pathway activity in hematopoietic, sometimes referred to as hematologic, cell malignancy. Activation of the Hh signaling pathway by sporadic mutations or in familial conditions such as Gorlin syndrome has been associated with tumorigenesis in skin, cerebellum, and skeletal muscle (see Bale, A. E. & Yu, K. P., The hedgehog pathway and basal cell carcinomas. *Hum. Mol. Genet.* 10, 757-62. (2001); Taipale, J. & Beachy, P. A. The Hedgehog and Wnt signalling pathways in cancer. *Nature* 411, 349-54. (2001); Wechsler-Reya, R. & Scott, M. P. The developmental biology of brain tumors. *Annu. Rev. Neurosci.* 24, 385-428 (2001); and Freestone, S. H. et al. Sonic hedgehog regulates prostatic growth and epithelial differentiation. *Dev Biol.* 264, 352-62 (2003)).

The present invention identifies arsenic trioxide (ATO) and other arsenic compounds as potent and specific inhibitors of the Hedgehog signaling pathway. ATO is an approved drug currently in use or treatment of leukemia. Based on the discovery that ATO is a Hedgehog pathway antagonist, its use can now be extended to any application where such inhibition is therapeutically useful, including many diseases associated with aberrant growth states that have been previously identified as requiring Hedgehog pathway activity. In addition, the present invention identifies hematopoietic malignancies as an additional general class of cancers in which Hedgehog pathway blockade may be therapeutically useful. Arsenic inhibition of Hedgehog pathway activity acts at the level of the Gli transcription factors. This is downstream of Smoothened, the site of action of most other pathway antagonists. This drug therefore may be useful for treatment of cancers caused by pathway activation at points downstream of Smoothened, as for example cancers caused by loss of Suppressor of Fused, by amplification of Gli genes, or by other genetic or epigenetic events that act downstream of Smoothened.

As disclosed herein, Hedgehog (Hh) pathway activity promotes changes in expression of genes known to modulate metastasis. Hematopoietic malignancy cells displayed elevated levels of Hh pathway activity that were suppressed by the Hh pathway antagonist cyclopamine. Cyclopamine also suppressed cell growth in vitro and caused regression of xenograft tumors in vivo. Unlike Gorlin syndrome tumors, Hh pathway activity and cell growth in hematopoietic malignancy cells is driven by endogenous expression of Hh ligands, as indicated by the presence of Sonic hedgehog (SHH) and Indian hedgehog (IHH) transcripts, by the pathway-inhibitory and growth-inhibitory activity of an Hh-neutralizing antibody, and by the dramatic growth-stimulatory activity of exogenously added Hh ligand. Accordingly, the present invention provides methods of treating a hematopoietic cell malignancy characterized by elevated Hh pathway activity as compared with a normal cell, as well as methods of determining whether a hematopoietic cell malignancy is amenable to treatment using an Hh pathway antagonist, and methods of identifying agents useful for treating such hematopoietic cell malignancies.

The term "agonist" refers to an agent or analog that is capable of inducing a full or partial pharmacological response. For example, an agonist may bind productively to a receptor and mimic the physiological reaction thereto. The term "antagonist" refers to an agent that is capable of inhibiting or otherwise reducing a pharmacological response. For example, an antagonist binds to receptors but does not provoke the normal biological response. Thus, an antagonist potentiates or recapitulates, for example, the bioactivity of patched, such as to repress transcription of target genes. The term "hedgehog antagonist" or "Hh antagonist" as used herein refers not only to any agent that may act by directly inhibiting the normal function of the hedgehog protein, but also to any agent that inhibits the hedgehog signaling pathway, and thus recapitulates the function of ptc. The term "hedgehog agonist" likewise refers to an agent which antagonizes or blocks the bioactivity of patched, such as to increase transcription of target genes. The hedgehog antagonists can be used to overcome a ptc gain-of-function and/or a smoothened loss-of-function, the latter also being referred to as 'smoothened agonists'.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The "gain-of-function" may include a loss of the ability of the ptc gene product to regulate the level of expression of Ci genes, e.g., Gli1, Gli2, and Gli3. The term 'hedgehog gain-of-function' is also used herein to refer to any similar cellular phenotype (e.g., exhibiting excess proliferation) which occurs due to an alteration anywhere in the hedgehog signal transduction pathway, including, but not limited to, a modification or mutation of hedgehog itself. For example, a tumor cell with an abnormally high proliferation rate due to activation of the hedgehog signaling pathway would have a 'hedgehog gain-of-function' phenotype, even if hedgehog is not mutated in that cell. 'Hedgehog loss-of-function' refers to the direct opposite of a hedgehog gain-of-function, e.g., an aberrant modification or mutation that results in a phenotype which resembles contacting a cell with an agent which blocks hedgehog function.

As used herein, reference to the "Hh pathway" means the Hedgehog signal transduction pathway. The Hh pathway is well known (see, e.g., U.S. Pat. No. 6,277,566 B1; U.S. Pat. No. 6,432,970 B2; Lum and Beachy, *Science* 304:1755-1759, 2004; and Bale and Yu, *Hum. Mol. Genet.* 10:757-762, 2001, each of which is incorporated herein by reference). Briefly, SHH, IHH and DHH are a family of secreted proteins that act as ligand (Hh ligands) to initiate the Hh pathway, which is involved in morphogenetic development and proliferation of cells in a variety of tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof.

The term "patched loss-of-function" refers to an aberrant modification or mutation of a ptc gene, or a decreased level of expression of the gene, which results in a phenotype which resembles contacting a cell with a hedgehog protein, e.g., aberrant activation of a hedgehog pathway. The 'gain-of-function' may include a loss of the ability of the ptc gene product to regulate the level of expression of Ci genes, e.g., Gli1, Gli2 and Gli3.

The term "smoothened gain-of-function" refers to an aberrant modification or mutation of a smo gene, or an increased level of expression of the gene, which results in a phenotype which resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., Nature 384: 177-179 (1996)). The smo gene is a segment-polarity gene required for the correct patterning of every segment in Drosophila (Alcedo et al., Cell 86: 221-232 (1996)). Human homologs of smo have been identified. See, for example, Stone et al., Nature 384:129-134 (1996), and GenBank accession no. U84401. The smoothened gene encodes an integral membrane protein with characteristics of heterotrimeric G-protein-coupled receptors; i.e., 7-transmembrane regions. This protein shows homology to the Drosophila Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, Nature 384: 119-120 (1996)). Rather, the binding of Sonic hedgehog (SHH) to its receptor, PTCH, is thought to prevent normal inhibition by PTCH of smoothened (SMO), a seven-span transmembrane protein.

Hh ligands bind to a receptor complex that includes Patched (PTCH; e.g., PTCH-1 in humans) and Smoothened (SMO), which are G-protein coupled receptor-like polypeptides. PTCH is an integral membrane protein with twelve transmembrane domains that acts as an inhibitor of SMO activation. Hh ligand binding to PTCH results in activation of SMO (see, e.g., Taipale et al., Nature 418:892-897, 2002, which is incorporated herein by reference), resulting in transduction of the signal and activation of the GLI family of transcriptional activators (e.g., GLI-1 and GLI-2, which act as transcriptional activators, and GLI-3, which acts as a transcriptional repressor), which are homologs of the Drosophila cubitis interruptis gene. Several kinases also are believed to be involved in the Hh pathway between SMO and the GLI transcription factors, including, for example, protein kinase A, which can inhibit GLI activity. Suppressor of Fused (SUFU) also interacts directly with GLI transcription factors to repress their activity. In addition, various transcriptional targets such as nestin and BMI-1 are regulated by Hh pathway activity.

The Hh signaling pathway specifies patterns of cell growth and differentiation in a wide variety of embryonic tissues. Mutational activation of the Hh pathway, whether sporadic or in Gorlin Syndrome, is associated with tumorigenesis in a limited subset of these tissues, predominantly skin, cerebellum, and skeletal muscle (Wechsler-Reya and Scott, The developmental biology of brain tumors. Ann. Rev. Neurosci. 24, 385-428 (2001); Bale and Yu, The hedgehog pathway and basal cell carcinomas. Hum. Mol. Genet. 10, 757-62 (2001)). Known pathway-activating mutations include those that impair the ability of PTCH (the target of Gorlin Syndrome mutations), a transporter-like Hh receptor (Taipale et al., Patched acts catalytically to suppress the activity of Smoothened. Nature 418, 892-7 (2002), to restrain Smoothened (SMO) activation of transcriptional targets via the GLI family of latent transcription factors. Binding of Hh ligand to PTCH is functionally equivalent to genetic loss of PTCH, in that pathway activation by either requires activity of SMO, a seven transmembrane protein that binds to and is inactivated by the pathway antagonist, cyclopamine (Chen et al., Inhibition of Hedgehog signaling by direct binding of cyclopamine to Smoothened. Genes Dev 16, 2743-8 (2002)).

The term "Hh pathway activity" is used herein to refer to the level of Hedgehog pathway signal transduction that is occurring in cells. Hh pathway activity can be determined using methods as disclosed herein or otherwise known in the art (see, e.g., Berman et al., Medulloblastoma growth inhibition by hedgehog pathway blockade. Science 297, 1559-61 (2002); Chen et al., Small molecule modulation of Smoothened activity. Proc Natl Acad Sci USA 99, 14071-6 (2002)). As used herein, the term "elevated" or "abnormally elevated", when used in reference to Hh pathway activity, means that the Hh pathway activity is increased above the level typically found in normal (i.e., not cancer) differentiated cells of the same type as the cells from which the tumor are derived. As such, the term "elevated Hh pathway activity" refers to the level of Hh pathway activity in prostate tumor cells as compared to corresponding normal cells. Generally, elevated Hh pathway activity is at least about 20% (e.g., 30%, 40%, 50%, 60%, 70%, or more) greater than the Hh pathway activity in corresponding normal cells. In this respect, it should be recognized that Hh pathway activity is determined with respect to a population of cells, which can be a population of tumor cells or a population of normal cells, and, therefore, is an average activity determined from the sampled population.

Reference herein to "corresponding normal cells" means cells that are from the same organ and/or of the same cell type as the cancer cell type. In one aspect, the corresponding normal cells comprise a sample of cells obtained from a healthy individual. Such corresponding normal cells can, but need not be, from an individual that is age-matched and/or of the same sex as individual providing the hematopoietic malignancy cells being examined. In another aspect, the corresponding normal cells comprise a sample of cells obtained from an otherwise healthy portion of tissue of a subject having a hematopoietic cell malignancy.

As used herein, the terms "sample" and "biological sample" refer to any sample suitable for the methods provided by the present invention. In one embodiment, the biological sample of the present invention is a tissue sample, e.g., a biopsy specimen such as samples from needle biopsy. In other embodiments, the biological sample of the present invention is a sample of bodily fluid, e.g., serum, plasma, urine, and ejaculate.

Accordingly, the invention provides methods of reducing or inhibiting Hh pathway activity and/or proliferation or metastasis of hematopoietic malignancy cells characterized by elevated or abnormally elevated Hh pathway activity. As used herein, the terms "reduce" and "inhibit" are used together because it is recognized that, in some cases, a decrease, for example, in Hh pathway activity can be reduced below the level of detection of a particular assay. As such, it may not always be clear whether the activity is "reduced" below a level of detection of an assay, or is completely "inhibited". Nevertheless, it will be clearly determinable, following a treatment according to the present methods, that the level of Hh pathway activity (and/or cell proliferation or metastasis) is at least reduced from the level before treatment. Generally, contact of hematopoietic malignancy cells having elevated Hh pathway activity with an Hh pathway antagonist reduces the Hh pathway activity by at least about 20% (e.g., 30%, 40%, 50%, 60%, 70%, or more). For example, the Hh pathway activity in a hematopoietic malignancy cell treated according to the present methods can be reduced to the level of Hh pathway activity typical of a corresponding normal cell.

A Hh pathway antagonist useful in a method of the invention generally acts at or downstream of the position in the Hh pathway that is associated with the elevated Hh pathway activity. For example, where elevated Hh pathway activity is ligand stimulated, the Hh antagonist can be selected based on the ability, for example, to sequester the Hh ligand (e.g., an antibody specific for the Hh ligand) or to reduce or inhibit binding of the Hh ligand to its receptor. Since Hh ligand activity is dependent on autoprocessing of the Hh ligand (e.g., SHH) into a C-terminal fragment, and an N-terminal fragment that is further modified by attachment of cholesterol and palmitate molecules (and constitutes the ligand; see, e.g., Mann and Beachy, *Ann. Rev. Biochem.* 73:891-923, 2004, which is incorporated herein by reference), ligand stimulated Hh pathway activity also can be reduced or inhibited by inhibiting autocleavage of the Hh ligand. Where elevated Hh pathway activity is due to an inactivating mutation of the Hh ligand receptor (e.g., PTCH), the Hh pathway antagonist can be selected based on the ability, for example, to sequester SMO (e.g., an antibody specific for SMO) or to reduce activity of a GLI transcription factor (e.g., a polynucleotide comprising a GLI regulatory element, which can act to sequester GLI); an anti-Hh ligand antibody may not necessarily reduce or inhibit elevated Hh pathway activity due to a mutation of PTCH because Hh ligand acts upstream of the defect in the Hh pathway. Further, steroidal alkaloids, such as cyclopamine, and derivatives thereof, and other small molecules such as SANT-1, SANT-2, SANT-3, and SANT-4 can reduce or inhibit elevated Hh pathway activity by directly repressing SMO activity. In addition, cholesterol can be required for Hh pathway activity and, therefore, agents that reduce the availability of cholesterol, for example, by removing it from cell membranes, can act as Hh pathway antagonists (see, e.g., Cooper et al., *Nat. Genet.* 33:508-513 (2003), which is incorporated herein by reference; see, also, Cooper et al., *Nat. Genet.* 34:113 (2003)).

A Hh pathway antagonist useful in a method of the invention can be any antagonist that interferes with Hh pathway activity, thereby decreasing the elevated or abnormally elevated Hh pathway in the hematopoietic malignancy cells. As such, the Hh pathway antagonist can be a peptide, a polynucleotide, a peptidomimetic, a small organic molecule, or any other molecule. In one embodiment, the Hh pathway antagonist is an arsenical agent, such as arsenic trioxide (ATO). Hh pathway antagonists are exemplified by antibodies, including anti-SHH antibodies, anti-IHH antibodies, and/or anti-DHH antibodies, each of which can bind to one or more Hh ligands and decrease ligand stimulated Hh pathway activity. Hh pathway antagonists are further exemplified by SMO antagonists such as steroidal alkaloids and derivatives thereof, including, for example, cyclopamine and jervine (see, e.g., Chen et al., *Genes Devel.* 16:2743-2748, 2002; and U.S. Pat. No. 6,432,970 B2, each of which is incorporated herein by reference), and SANT-1, SANT-2, SANT-3, and SANT-4 (see Chen et al., *Proc. Natl. Acad. Sci., USA* 99:14071-14076, 2002, which is incorporated herein by reference); triparanol provides another example of an agent that can act as an Hh pathway antagonist (see, e.g., U.S. Pat. No. 6,432,970 B2, incorporated herein by reference). As exemplified herein, an anti-SHH antibody and cyclopamine effectively reduced elevated Hh pathway activity in hematopoietic malignancy cells and reduced viability of the cells in vitro, and cyclopamine suppressed growth of prostate tumor xenografts in nude mice.

It is, therefore, specifically contemplated that ATO and other arsenicals which interfere with Hedgehog signal transduction activity of hedgehog, ptc, smoothened, or other pathway components will likewise be capable of inhibiting proliferation (or other biological consequences) in normal cells and/or cells having a patched loss-of-function phenotype, a hedgehog gain-of-function phenotype, or a smoothened gain-of-function phenotype, or any other effect on pathway components upstream of or at the level of Gli. Thus, the methods of the present invention include the use of arsenicals in the regulation of repair and/or functional performance or malignant growth of a wide range of cells, tissues and organs, including normal cells, tissues, and organs, as well as those having the phenotype of ptc loss-of-function, hedgehog gain-of-function, or smoothened gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the subject methods can be performed on cells that are provided in culture (in vitro), or on cells in a whole animal (in vivo).

As such, the methods of the invention can be used to treat any disorder involving abnormal or inappropriate Hedgehog pathway activity. In one embodiment, the method can be used to treat cancers arising in epithelia of endodermally-derived organs including small cell lung cancer, and carcinomas of the esophagus, stomach, pancreas, biliary tract, prostate, and bladder. Other indications that can be treated by the methods of the invention include, but are not limited to, basal cell carcinoma, medulloblastoma, rhabdomyosarcoma, and ovarian cancer. In other embodiments, this invention may find application in the treatment of other conditions such as psoriasis and hirsutism.

Because ATO is effectively used in promyelocytic leukemia, the work demonstrated herein indicates that Hedgehog pathway blockade may be generally useful for treatment of leukemias arising within a broad range of hematopoietic malignancies including myeloid leukemias. In one embodiment, this invention contemplates the use of ATO and other arsenicals in a broad range of hematopoietic malignancies, including diseases in the myeloid as well as lymphoid lineages. In another embodiment, this invention contemplates the use of ATO and other arsenicals in a combination with other drugs that inhibit Hedgehog pathway activity by the same or by other mechanisms either at the same Gli level or at different points in the Hh pathway as a means to permit use of lower concentrations that reduce toxicity of either compound. In another embodiment, the invention contemplates use of two or more Hh antagonists that inhibit the Hh pathway at different points of the pathway to ensure a more complete blockage of the pathway, in case one point is "leaky."

In one embodiment, the Hh antagonists are administered in combination with an anti-inflammatory agent, antihistamines, chemotherapeutic agent, immunomodulator, therapeutic antibody or a protein kinase inhibitor, e.g., a tyrosine kinase inhibitor, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxydaunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

Thus, in one aspect, the present invention provides a method of ameliorating hematopoietic cell malignancy comprising cells characterized by elevated or abnormally elevated Hh pathway activity in a subject. As used herein, the term "ameliorate" means that the clinical signs and/or the symptoms associated with the hematopoietic cell malignancy are lessened. The signs or symptoms to be monitored will be characteristic of a particular hematopoietic cell malignancy and will be well known to the skilled clinician, as will the methods for monitoring the signs and conditions.

Hematopoietic malignancy cells for which Hh pathway activity and cell proliferation or metastasis can be reduced or inhibited can be any hematopoietic malignancy cells that are characterized, at least in part, by Hh pathway activity that is elevated above levels that are typically found in a corresponding normal cell. As such, hematopoietic cell malignancy, is exemplified herein by B cell lymphoma, cancer stem cells of multiple myeloma, lymphoid leukemia, promyelocytic leukemia (PML), chronic myelogenous leukemia (CML), myeloid leukemia, and acute myeloid leukemia (AML).

An agent useful in a method of the invention can be any type of molecule, for example, a polynucleotide, a peptide, a peptidomimetic, peptoids such as vinylogous peptoids, a small organic molecule, or the like, and can act in any of various ways to reduce or inhibit elevated Hh pathway activity, and may be used in combination with one or more therapeutic agents, immunomodulatory agents, antibodies, enzyme inhibitors, or steroidal alkaloids, or derivatives thereof. Further, the agent (e.g., an Hh pathway antagonist) can be administered in any way typical of an agent used to treat the particular type of hematopoietic cell malignancy or under conditions that facilitate contact of the agent with the target hematopoietic malignancy cells and, if appropriate, entry into the cells. Entry of a polynucleotide agent into a cell, for example, can be facilitated by incorporating the polynucleotide into a viral vector that can infect the cells. If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell.

Generally, the agent useful in a method of the invention is formulated in a composition (e.g., a pharmaceutical composition) suitable for administration to the subject, which can be any vertebrate subject, including a mammalian subject (e.g., a human subject). Such formulated agents are useful as medicaments for treating a subject suffering from a hematopoietic cell malignancy that is characterized, in part, by elevated or abnormally elevated Hh pathway activity.

The terms "administration" or "administering" is defined to include the act of providing an agent of the invention or pharmaceutical composition to the subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration. Thus, the antagonists of the invention may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Pharmaceutically acceptable carriers useful for formulating an agent for administration to a subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second (or more) compound (s) such as a diagnostic reagent, nutritional substance, toxin, or therapeutic agent, for example, a cancer chemotherapeutic agent and/or vitamin(s).

The agent, which acts as an Hh pathway antagonist to reduce or inhibit the elevated Hh pathway activity, can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225, 212, each of which is incorporated herein by reference) are an example of such encapsulating materials particularly useful for preparing a pharmaceutical composition useful for practicing a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.* 91:2580-2585 (1993), which is incorporated herein by reference). In addition, a polynucleotide agent can be introduced into a cell using, for example, adenovirus-polylysine DNA complexes (see, for example, Michael et al., *J. Biol. Chem.* 268:6866-6869 (1993), which is incorporated herein by reference).

The route of administration of a composition containing the Hh pathway antagonist will depend, in part, on the chemical structure of the molecule. Polypeptides and polynucleotides, for example, are not particularly useful when administered orally because they can be degraded in the digestive tract. However, methods for chemically modifying polynucleotides and polypeptides, for example, to render them less susceptible to degradation by endogenous nucleases or proteases, respectively, or more absorbable through the alimentary tract are well known (see, for example, Blondelle et al., *Trends Anal. Chem.* 14:83-92, 1995; Ecker and Crook, *BioTechnology*, 13:351-360, 1995). For example, a peptide agent can be prepared using D-amino acids, or can contain one or more domains based on peptidomimetics, which are organic molecules that mimic the structure of peptide domain; or based on a peptoid such as a vinylogous peptoid. Where the agent is a small organic molecule such as a steroidal alkaloid (e.g., cyclopamine), it can be administered in a form that releases the active agent at the desired position in the body (e.g., the stomach), or by injection into a blood vessel that the agent circulates to the target cells (e.g., hematopoietic malignancy cells).

Regardless of the route of administration selected, the compounds of the present invention, which may be used in a suitable hydrated form, and/or the pharmaceutical compositions of the present invention, are formulated into pharmaceutically acceptable dosage forms such as described herein or by other conventional methods known to those of skill in the art.

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the Hh pathway antagonist to treat a hematopoietic cell malignancy in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day which can be administered in single or multiple doses.

If desired, the effective daily dose of the active compound may be administered as two, three, four, five, six or more sub-doses administered separately at appropriate intervals throughout the day, optionally, in unit dosage forms. There may be a period of no administration followed by another regimen of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

When other therapeutic agents are employed in combination with the compounds of the present invention they may be used for example in amounts as noted in the Physician Desk Reference (PDR) or as otherwise determined by one having ordinary skill in the art.

The term "effective amount" is defined as the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality. For example, a "therapeutically effective amount" of, e.g., a Hh antagonist, with respect to the subject method of treatment, refers to an amount of the antagonist in a preparation which, when applied as part of a desired dosage regimen brings about, e.g., a change in the rate of cell proliferation and/or the state of differentiation and/or the rate of metastasis of a cell and/or rate of survival of a cell according to clinically acceptable standards for the disorder to be treated.

The invention also provides a method of determining whether hematopoietic malignancy cells in a subject are amenable to treatment with a Hh pathway antagonist as disclosed herein. The method can be performed, for example, by measuring the level Hh pathway activity in a hematopoietic malignancy cell sample of a subject to be treated, and determining that Hh pathway activity is elevated or abnormally elevated as compared to the level of Hh pathway activity in corresponding normal cells, which can be a sample of normal (i.e., not cancer) cells of the subject having the hematopoietic cell malignancy. Detection of elevated or abnormally elevated level Hh pathway activity in the hematopoietic malignancy cells as compared to the corresponding normal cells indicates that the subject can benefit from treatment with an Hh pathway antagonist.

Elevated or abnormally elevated Hh pathway activity can be determined by measuring elevated expression of one or more (e.g., 1, 2, 3, or more) Hh pathway polypeptide(s), including, for example, one or more Hh ligands (e.g., SHH, IHH, and/or desert hedgehog), Hh ligand receptors (e.g., PTCH), or transcription factors (a GLI family member), or a combination of such Hh pathway polypeptides. The elevated expression can be detected by measuring the level of a polynucleotide encoding the Hh pathway polypeptide (e.g., RNA) using, for example, a hybridization assay, a primer extension assay, or a polymerase chain reaction (PCR) assay (e.g., a reverse transcription-PCR assay); or by measuring the level the Hh pathway polypeptide(s) using, for example, an immunoassay or receptor binding assay. Alternatively, or in addition, elevated activity of one or more (e.g., 1, 2, 3, or more) Hh pathway polypeptide(s) can be determined. For example, elevated activity of Hh pathway transcription factor (e.g., a GLI family member) can be detected by measuring increased binding activity of the transcription factor to a cognate transcription factor regulatory element (e.g., using an electrophoretic mobility shift assay), or by measuring increased expression of a reporter gene comprising a cognate transcription factor regulatory element. Expression of an Hh pathway polypeptide having an inactivating mutation can be identified using, for example, an antibody that specifically binds to the mutant, but not to the normal (wild type), Hh polypeptide, wherein the mutation is associated with elevated Hh pathway activity. For example, common mutations that result in expression of an inactivated PTCH can define unique epitopes that can be targeted by diagnostic antibodies that specifically bind the mutant, but not wild type, PTCH protein.

The method of identifying hematopoietic cell malignancy amenable to treatment with a Hh pathway antagonist can further include contacting cells of the sample with at least one Hh pathway antagonist, and detecting a decrease in Hh pathway activity in the cells following contact. The decreased Hh pathway activity can be detected, for example, by measuring decreased expression of a reporter gene regulated by an Hh pathway transcription factor, or by detecting a decrease in proliferation or metastasis of the hematopoietic malignancy cells. Such a method provides a means to confirm that the hematopoietic cell malignancy is amenable to treatment with an Hh pathway antagonist. Further, the method can include testing one or more different Hh pathway antagonists, either alone or in combination, thus providing a means to identify one or more Hh pathway antagonists useful for treating the particular hematopoietic cell malignancy being examined. Accordingly, the present invention also provides a method of identifying an agent useful for treating a hematopoietic cell malignancy characterized by elevated Hh pathway activity.

The method of identifying an agent useful for treating a hematopoietic cell malignancy provides a means for practicing personalized medicine, wherein treatment is tailored to a subject based on the particular characteristics of the hematopoietic cell malignancy in the subject. The method can be practiced, for example, by contacting a sample of cells of a hematopoietic cell malignancy with at least one test agent, wherein a decrease in Hh pathway activity in the presence of the test agent as compared to Hh pathway activity in the absence of the test agent identifies the agent as useful for treating the hematopoietic cell malignancy. The sample of cells examined according to the present method can be obtained from the subject to be treated, or can be cells of an established hematopoietic malignancy cell line of the same type of cancer as that of the subject. In one aspect, the established hematopoietic malignancy cell line can be one of a panel of such cell lines, wherein the panel can include different cell lines of the same type of hematopoietic malignancy and/or different cell lines of different hematopoietic cell malignancies. Such a panel of cell lines can be useful, for example, to practice the present method when only a small number of hematopoietic malignancy cells can be obtained from the subject to be treated, thus providing a surrogate sample of the subject's cancer, and also can be useful to include as control samples in practicing the present methods.

The present methods can be practiced using test agents that are known to be effective in treating a hematopoietic cell malignancy having elevated Hh pathway activity (e.g., an arsenical agent, a steroidal alkaloid such as cyclopamine or jervine; and/or other SMO antagonist such as SANT-1 or SANT-2; and/or an anti-Hh ligand antibody such as an anti-SHH antibody) in order to identify one or more agents that are particularly useful for treating the hematopoietic cell malignancy being examined, or using test agents that are being examined for effectiveness. In addition, the test agent(s) examined according to the present method can be any type of compound, including, for example, a peptide, a polynucleotide, a peptidomimetic, or a small organic molecule, and can be one or a plurality of similar but different agents such as a combinatorial library of test agents, which can be a randomized or biased library or can be a variegated library based on known effective agent such as the known Hh pathway antagonist, cyclopamine (see, for example, U.S. Pat. Nos. 5,264, 563; and 5,571,698, each of which is incorporated herein by reference). Methods for preparing a combinatorial library of molecules, which can be tested for Hh pathway antagonist activity, are well known in the art and include, for example, methods of making a phage display library of peptides, which can be constrained peptides (see, for example, U.S. Pat. Nos. 5,622,699; 5,206,347; Scott and Smith, *Science* 249:386-390, 1992; Markland et al., *Gene* 109:13-19, 1991; each of which is incorporated herein by reference); a peptide library (U.S. Pat. No. 5,264,563, which is incorporated herein by reference); a peptidomimetic library (Blondelle et al., supra, 1995; a nucleic acid library (O'Connell et al., *Proc. Natl. Acad. Sci., USA* 93:5883-5887, 1996; Tuerk and Gold, *Science* 249:505-510, 1990; Gold et al., *Ann. Rev. Biochem.* 64:763-797, 1995; each of which is incorporated herein by reference; each of which is incorporated herein by reference); an oligosaccharide library (York et al., *Carb. Res.* 285:99-128, 1996; Liang et al., *Science* 274:1520-1522, 1996; Ding et al., *Adv. Expt. Med. Biol.* 376:261-269, 1995; each of which is incorporated herein by reference); a lipoprotein library (de Kruif et al., *FEBS Lett.* 399:232-236, 1996, which is incorporated herein by reference); a glycoprotein or glycolipid library (Karaoglu et al., *J. Cell Biol.* 130:567-577, 1995, which is incorporated herein by reference); or a chemical library containing, for example, drugs or other pharmaceutical agents (Gordon et al., *J. Med. Chem.* 37:1385-1401, 1994; Ecker and Crooke, supra, 1995; each of which is incorporated herein by reference).

The method of identifying an agent useful for treating a hematopoietic cell malignancy characterized by having elevated Hh pathway activity can performed by contacting the sample of cells ex vivo, for example, in a culture medium or on a solid support. Alternatively, or in addition, the method can be performed in vivo, for example, by transplanting hematopoietic malignancy cells into a test animal (e.g., a nude mouse), and administering the test agent to the test animal. An advantage of the in vivo assay is that the effectiveness of a test agent can be evaluated in a living animal, thus more closely mimicking the clinical situation. Since in vivo assays generally are more expensive, they can be particularly useful as a secondary screen, following the identification of "lead" agents using an in vitro method.

When practiced as an in vitro assay, the methods can be adapted to a high throughput format, thus allowing the examination of a plurality (i.e., 2, 3, 4, or more) of cell samples and/or test agents, which independently can be the same or different, in parallel. A high throughput format provides numerous advantages, including that test agents can be tested on several samples of cells from a single patient, thus allowing, for example, for the identification of a particularly effective concentration of an agent to be administered to the subject, or for the identification of a particularly effective agent to be administered to the subject. As such, a high throughput format allows for the examination of two, three, four, etc., different test agents, alone or in combination, on the hematopoietic malignancy cells of a subject such that the best (most effective) agent or combination of agents can be used for a therapeutic procedure. Further, a high throughput format allows, for example, control samples (positive controls and/or negative controls) to be run in parallel with test samples, including, for example, samples of cells known to be effectively treated with an agent being tested.

A high throughput method of the invention can be practiced in any of a variety of ways. For example, different samples of cells obtained from different subjects can be examined, in parallel, with same or different amounts of one or a plurality of test agent(s); or two or more samples of cells obtained from one subject can be examined with same or different amounts of one or a plurality of test agent. In addition, cell samples, which can be of the same or different subjects, can be examined using combinations of test agents and/or known effective agents. Variations of these exemplified formats also can be used to identifying an agent or combination of agents useful for treating a hematopoietic cell malignancy characterized as having elevated Hh pathway activity.

When performed in a high throughput (or ultra-high throughput) format, the method can be performed on a solid support (e.g., a microtiter plate, a silicon wafer, or a glass slide), wherein samples to be contacted with a test agent are positioned such that each is delineated from each other (e.g., in wells). Any number of samples (e.g., 96, 1024, 10,000, 100,000, or more) can be examined in parallel using such a method, depending on the particular support used. Where samples are positioned in an array (i.e., a defined pattern), each sample in the array can be defined by its position (e.g., using an x-y axis), thus providing an "address" for each sample. An advantage of using an addressable array format is that the method can be automated, in whole or in part, such that cell samples, reagents, test agents, and the like, can be dispensed to (or removed from) specified positions at desired times, and samples (or aliquots) can be monitored, for example, for Hh pathway activity and/or cell viability.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Figure 2:
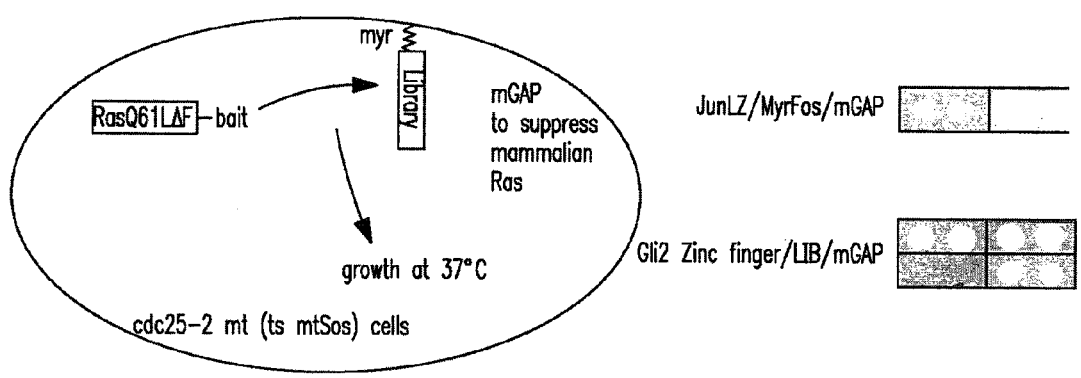
FIG. 2 is a pictorial diagram showing Ras Recruitment System (RRS) yeast 2-hybrid screening. Gli2 zinc fingers 1-5 inter-act with Asna1, a homolog of the ATPase subunit of bacterial arsenic transporter. Note that RRS forces the interaction to occur on the plasma membrane, which enabled us to perform two-hybrid screening with transcription factor baits without having high false positives.

This example demonstrates the Hedgehog pathway-inhibitory properties of ATO, as observed in a study of regulatory mechanisms of Gli activity by screening for interaction partners. The Gli proteins are the major transcriptional effectors of vertebrate Hedgehog signaling pathway. Five zinc fingers are present in Gli proteins, although only the first three are involved in base-specific DNA contacts (FIG. 1). This raises the possibility that the remaining zinc fingers, which are highly conserved, might be the target of regulatory interactions with other proteins. To shed light on the regulatory mechanisms of Gli activity, protein interaction partners of the Gli zinc fingers were identified by yeast two-hybrid screening using the Ras Recruitment System (RRS; FIG. 2; Curr Biol 1998, 8: 1121-1124). Accordingly, a new Gli zinc finger binding protein Asna1, which is a homolog of the ATPase subunit of a bacterial arsenic transporter (Gene 2001, 272: 291-299) was identified. Asna1 has recently been shown to play important roles in insertion of tail-anchored proteins that have a C-terminal transmembrane domain into ER (Cell 2007, 128: 1147-1159) and also in insulin secretion (Cell 2007, 128: 577-587). Since arsenic compounds stimulate ATPase activities of Asna1 (J Biol Chem 1998, 273: 22173-22176), it was tested whether these compounds affect mammalian Hedgehog pathway activity.

Figure 3:
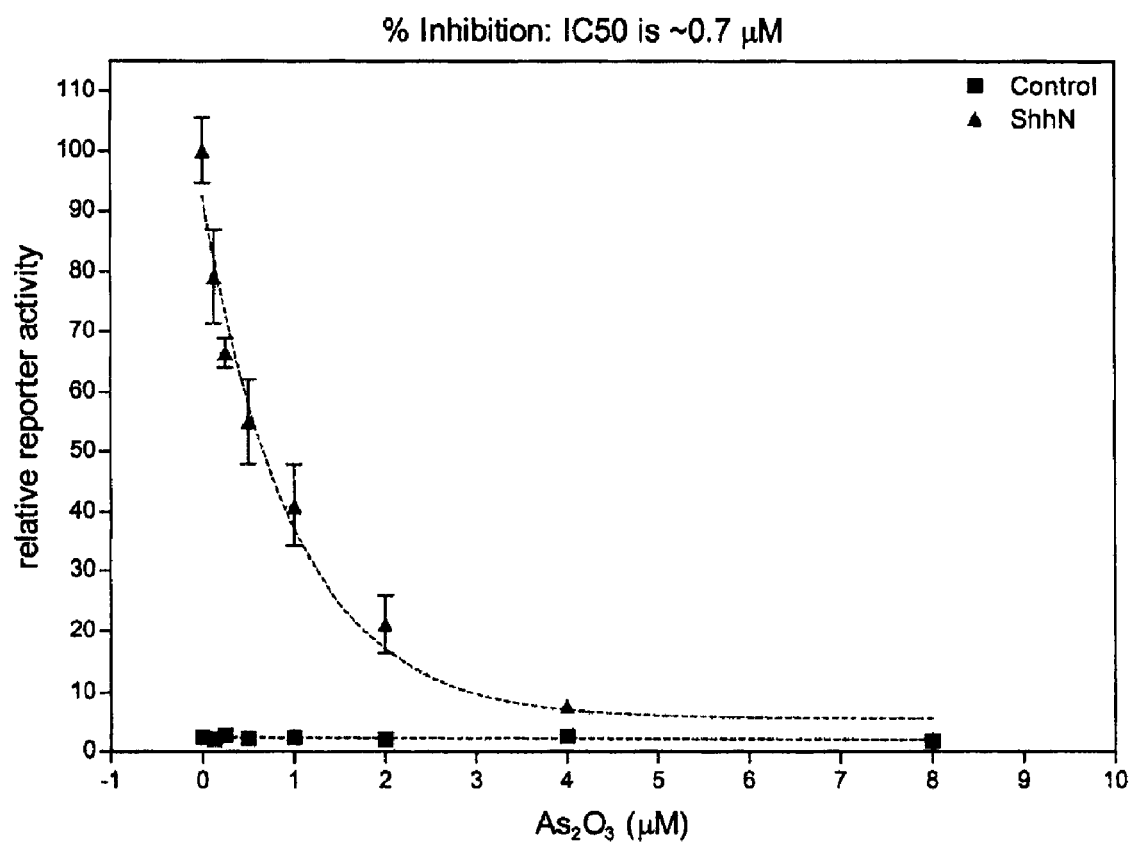
FIG. 3 is a graphical diagram showing that the anti-leukemic drug ATO inhibits Hh pathway in a dose-dependent manner. NIH3T3 cells were transfected with a Hh activity reporter consisting of 8 tandemly repeated Gli responsive elements coupled to luciferase (8×Gli-luciferase) and increasing concentrations of arsenic trioxide were applied in the presence or absence of ShhN-conditioned medium.

The assay for Hh pathway effects proceeded essentially as described in Chen, J. K., Taipale, J., Young, K. E., Maiti, T. & Beachy, P. A. (2002). Small molecule modulation of Smoothened activity. *Proc Natl Acad Sci USA* 99, 14071-6. Briefly, compounds being tested were added to a cultured cell-based Sonic hedgehog (Shh) signaling assay. This assay utilized cells with a stably integrated firefly luciferase reporter that is responsive to ShhN signaling. These cells also contain a stably integrated, constitutively expressed *Renilla luciferase* gene that can be used for normalization of response to Shh and to monitor cell health. As shown in FIG. 3, arsenic compounds shut down Shh signal response.

Figure 4:
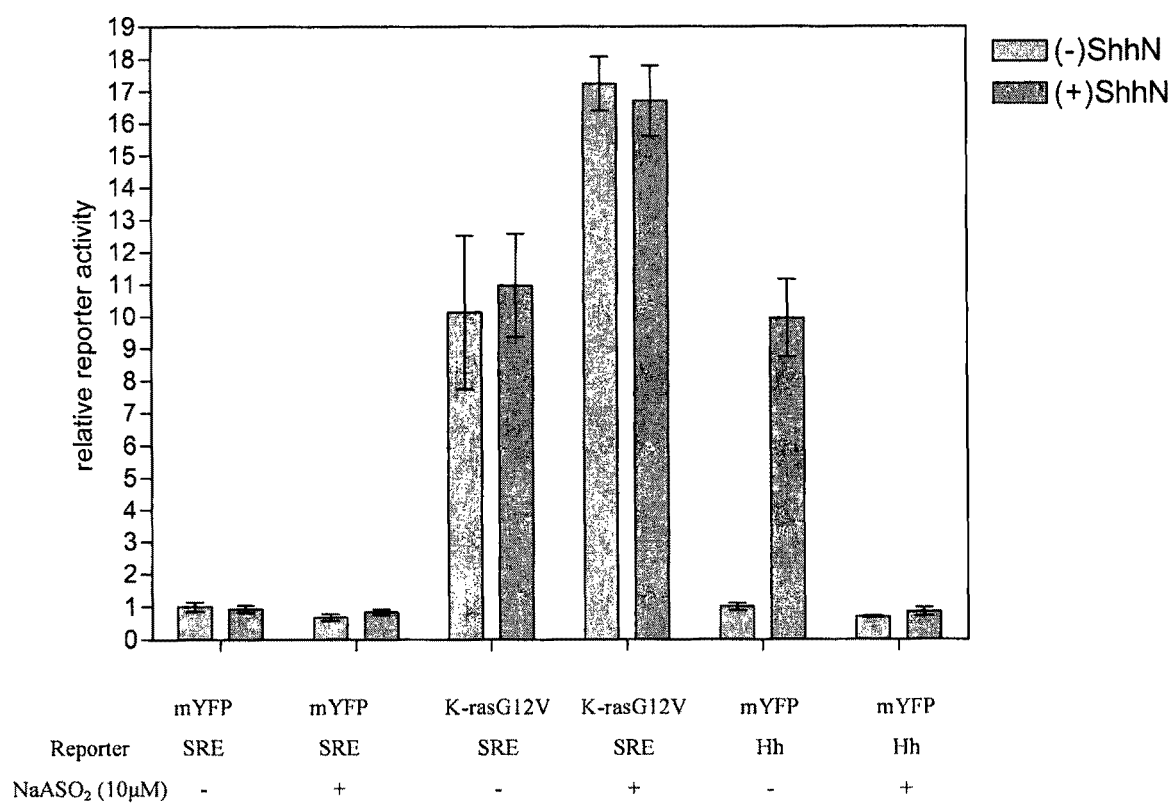
FIG. 4 is a graphical diagram showing that arsenite inhibits Hh signaling whereas it augments K-ras pathway. To determine the specificity of arsenic action on Hh pathway, 3T3 cells were contransfected with mYFP or constitutively active K-rasG12V with reporters as indicated. SRE reporter (serum responsive element coupled to luciferase) was used as an indicator of ras pathway activity.

To assess the specificity of the arsenic effect on Hedgehog pathway signaling, 3T3 cells were co-transfected with mYFP or constitutively active K-rasG12V with reporters as indicated. SRE reporter (serum responsive element coupled to luciferase) was used as an indicator of ras pathway activity. It was found that arsenic did not inhibit, and in fact stimulated the K-ras pathway, as monitored by luciferase activity from the serum responsive element (SRE)-containing reporter (FIG. 4). Importantly, in this experiment a distinct arsenic compound, $NaAsO_2$, was used to indicate that a range of arsenicals in addition to ATO would also be effective in Hedgehog pathway inhibition.

Figure 5:
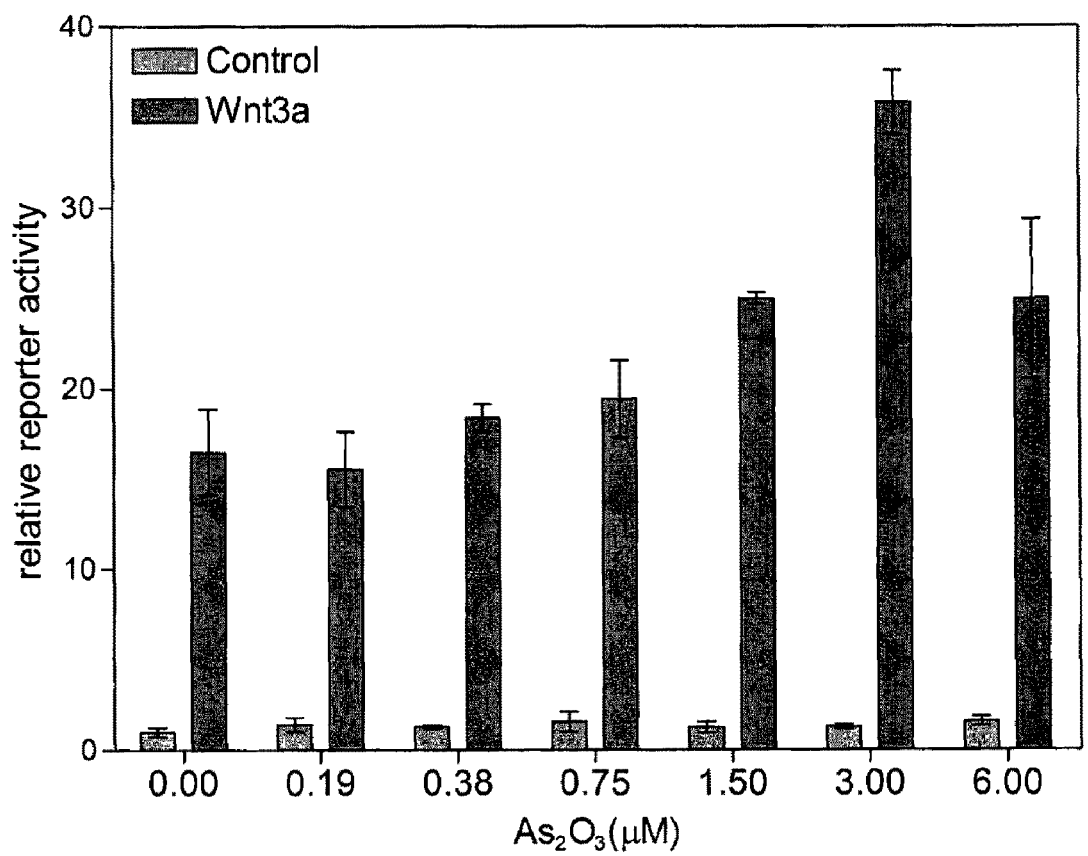
FIG. 5 is a graphical diagram showing that ATO does not inhibit the Wnt pathway. 3T3 cells were transfected with a Wnt reporter (7×TCF/LEF-luciferase) and treated with increasing concentrations of ATO in the presence or absence of Wnt3a-conditioned medium.

To further assess the specificity of the arsenic effect on Hedgehog pathway signaling, 3T3 cells were transfected with a Wnt reporter (7×TCF/LEF-luciferase) and treated with increasing concentrations of ATO in the presence or absence of Wnt3a-conditioned medium. It was found that arsenic compounds did not affect Wnt signaling (FIG. 5).

Figure 6A:
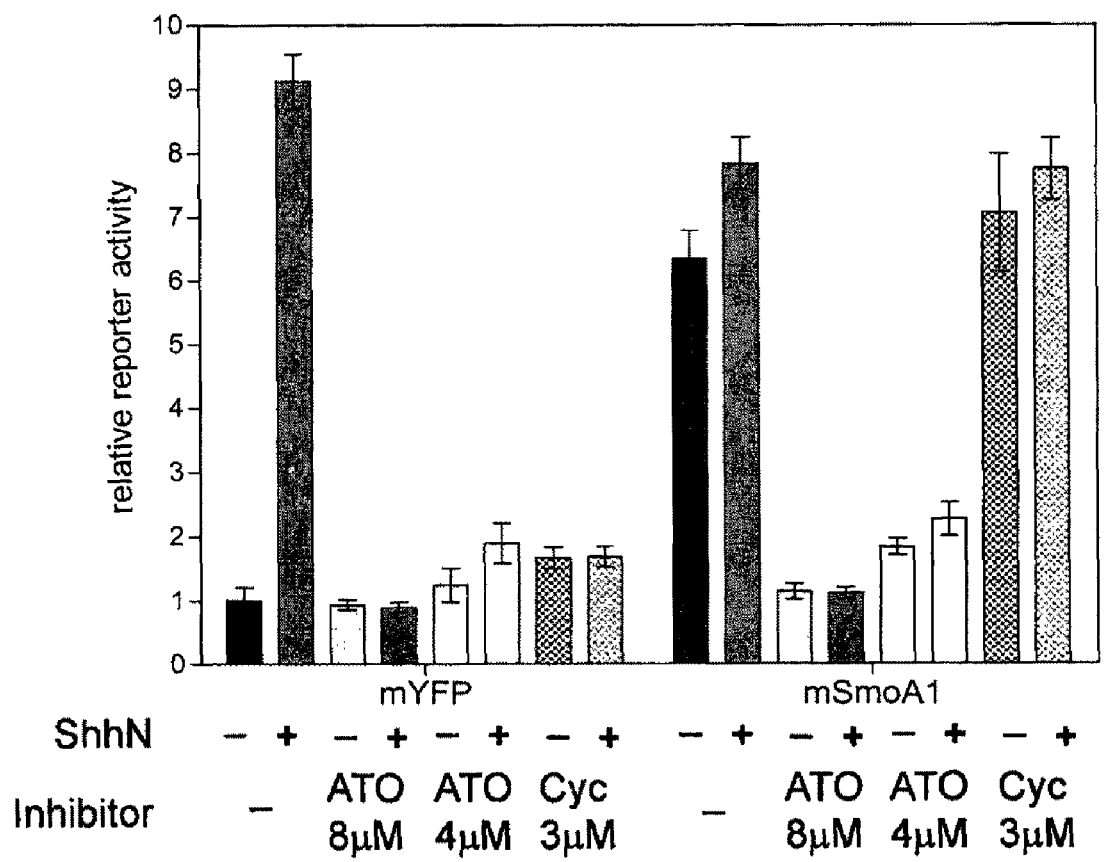
FIGS. 6A and 6B are graphical diagrams showing that ATO acts at the level of Gli. 3T3 cells were cotransfected with Hh reporter and either SmoA1 (FIG. 6A), Gli2, or Gli1 (FIG. 6B) and treated with ATO or cyclopamine in the presence or absence of ShhN. ATO suppressed but cyclopamine was unable to block the pathway activity induced by SmoA1 or Gli overexpression.
Figure 6B:
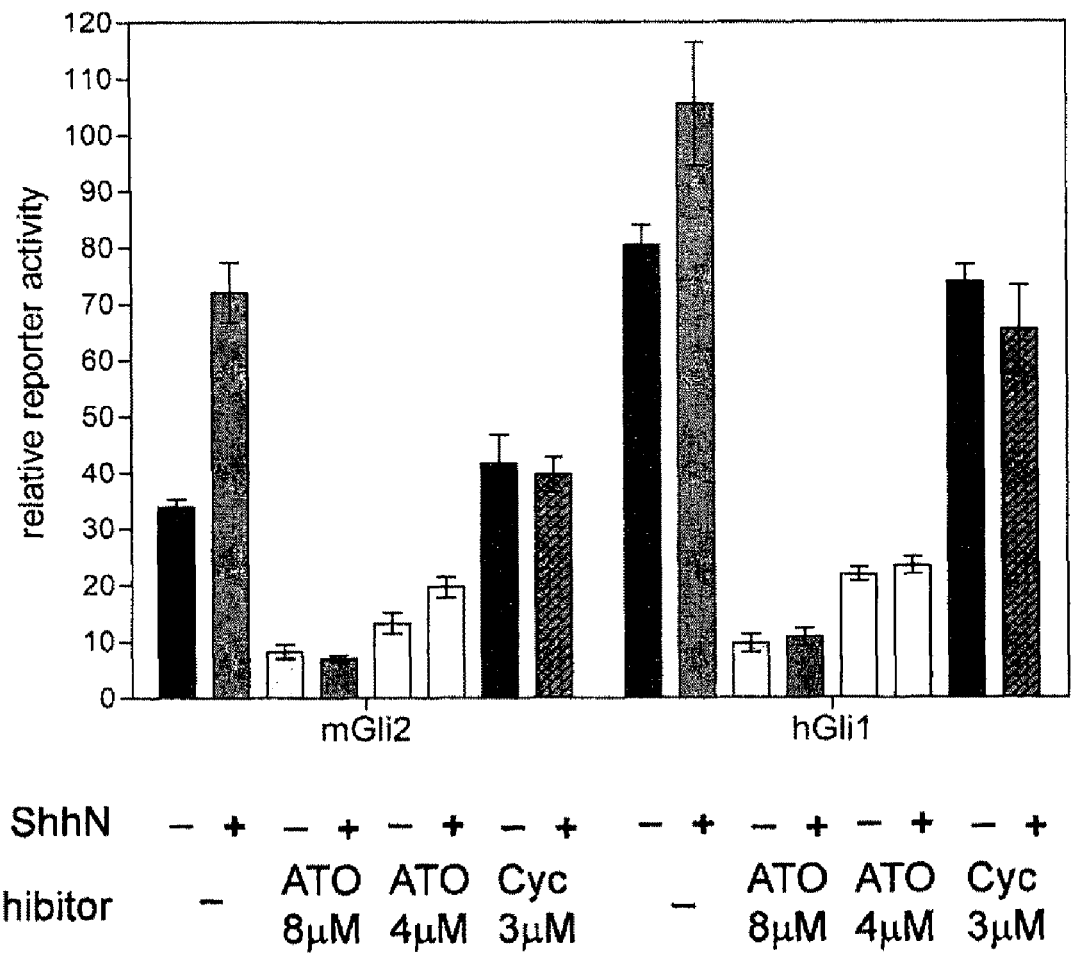

To shed light on the mechanism of arsenic inhibition of Hedgehog pathway activity, 3T3 cells were co-transfected with Hh reporter and either SmoA1, Gli2, or Gli1 and treated with ATO or cyclopamine in the presence or absence of ShhN. Cyclopamine was unable to block the pathway activity induced by SmoA1 or Gli over-expression (FIGS. 6A and 6B). ATO, however, dramatically inhibited reporter activity produced by expression of SmoA1, Gli2, or Gli1 (FIGS. 6A and B). This indicates that arsenic acts within the pathway by targeting either the downstream effector Gli or both Gli and some other upstream component.

Figure 7:
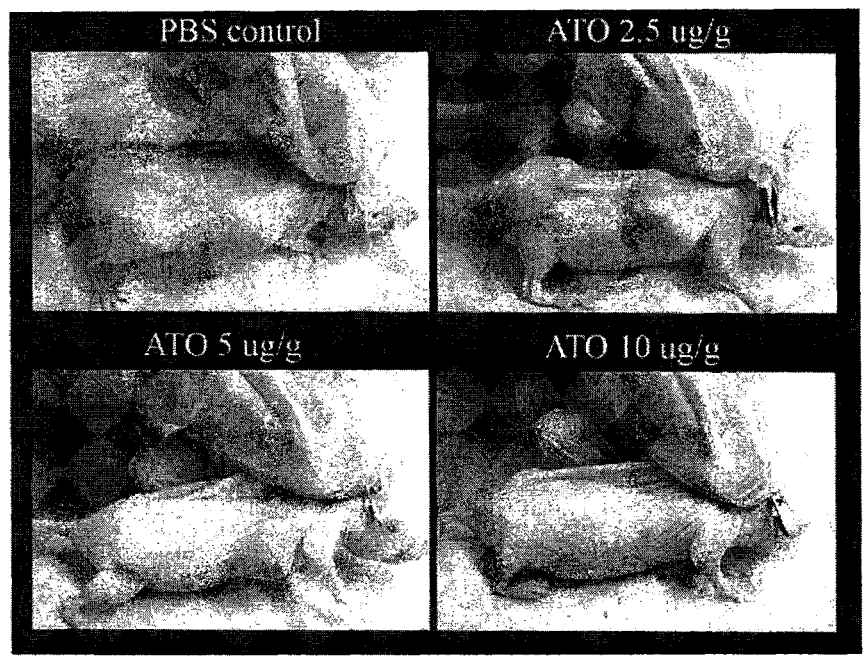
FIG. 7 is a pictorial and a graphical diagram showing that ATO inhibits growth of Hh activity-induced medulloblastoma allografts in nude mice. Primary medulloblastoma from Ptch+/−p53−/− mice were dissected and injected into athymic nude mice. The mice were injected daily with either control PBS or 3 different doses of ATO intraperitoneally.
Figure 7:
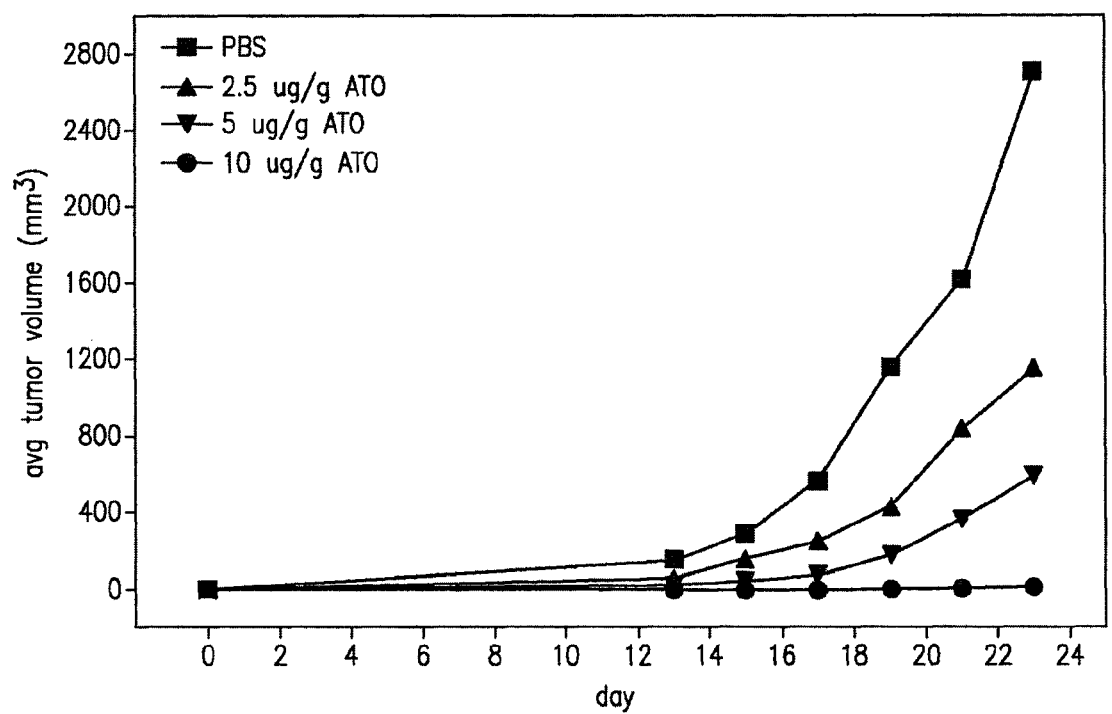

The activity of ATO was then tested in vivo in a well-established model of a tumor that is dependent on Hh pathway activity for growth. In this model, primary medulloblastoma cells from Ptch+/−p53−/− mice were dissected and injected into athymic nude mice. The mice were then injected daily with either control PBS or 3 different doses of ATO intraperitoneally. It was found that ATO suppressed tumor allograft growth in a concentration dependent manner, with complete growth suppression noted at the highest concentration tested (FIG. 7).

Figure 8:
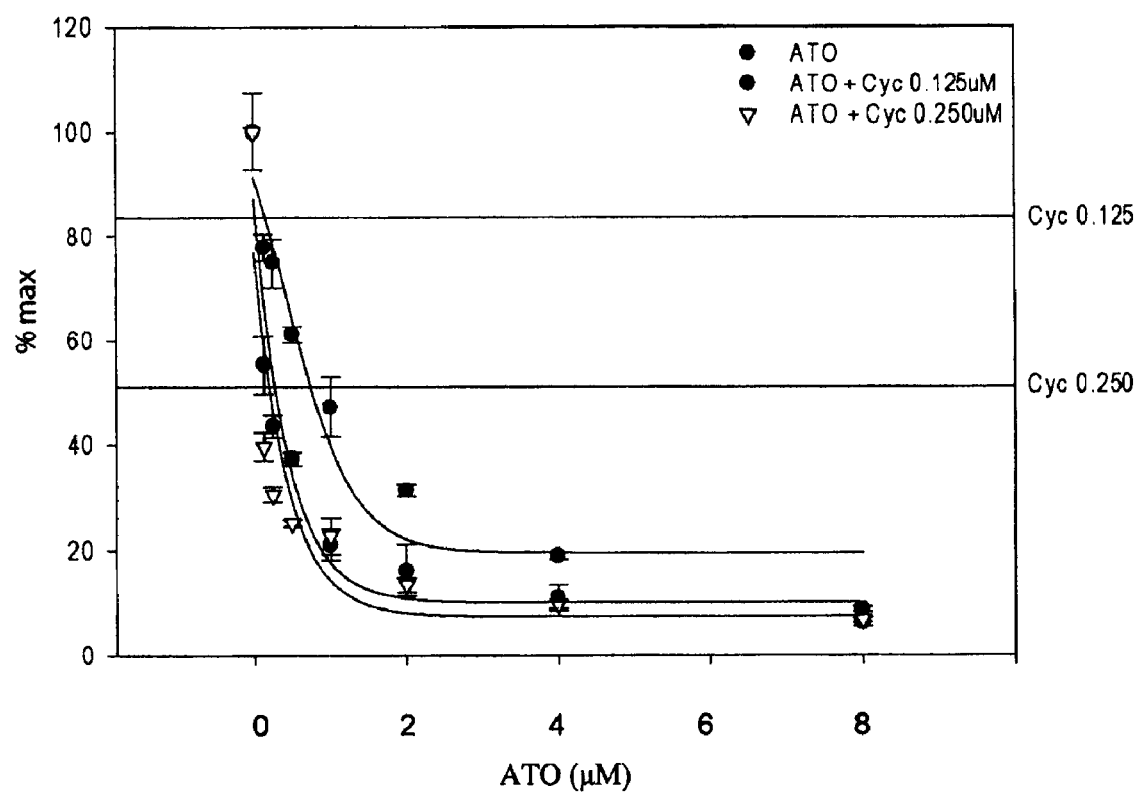
FIG. 8 is a graphical diagram showing that ATO cooperates with cyclopamine to suppress Hh pathway. 3T3 cells were transfected with 8×Gli-luciferase reporter and treated with increasing concentrations of ATO together with two fixed concentrations of cyclopamine in the presence of ShhN.

To test the possibility that ATO may be effective at reduced concentrations when combined with other pathway antagonists, a series of ATO concentrations were combined with cyclopamine at fixed concentrations of 0.25 and 0.125 μM in the 3T3 cultured cell assay. Cyclopamine inhibits Hedgehog signaling by binding to Smoothened with an $IC_{50}$ of ~0.25 μM. It was noted that a significantly improved effect of ATO at lower concentrations (FIG. 8), suggesting that any toxicity of ATO (or other pathway antagonists) might be reduced by combining antagonists with effects at distinct points in the pathway.

Medulloblastoma cells from mice Asna1 as a binding partner of Gli zinc fingers by Ras Recruitment System yeast two-hybrid screening. Asna1 is a homolog of the ATPase subunit of bacterial arsenic transporter and the ATPase is known to be activated by arsenic compounds. Treatment of arsenic trioxide (ATO), an effective therapeutic agent for acute promyelocytic leukemia, specifically inhibited Hh pathway in a dose-dependent manner. ATO inhibited the pathway activity induced by Hedgehog, SmoA1, Gli1 or Gli2 overexpression, suggesting that it acts at the level of Gli. ATO also suppressed growth of Hh-induced medulloblastoma allograft in nude mice. These results suggest that ATO has a therapeutic potential as a Hh antagonist.

Although the invention has been described with reference to the above example, it will be understood that modifications and variations are encompassed within the spirit and scope of the invention. Accordingly, the invention is limited only by the following claims.

What is claimed is:

1. A method of treating hematopoietic cell malignancy in a subject comprising administering to the subject at least one Hh pathway antagonist to reduce Hh pathway activity, wherein the at least one Hh pathway antagonist comprises arsenic trioxide (ATO) or $NaAsO_2$.

2. The method of claim 1, wherein the hematopoietic cell malignancy is leukemia.

3. The method of claim 2, wherein the leukemia is selected from PML, AML, or CML.

4. The method of claim 3, wherein the leukemia is PML.

5. The method of claim 1, wherein the Hh pathway antagonist is an arsenical agent.

6. The method of claim 5, wherein the arsenical agent is arsenic trioxide (ATO) or $NaAsO_2$.

7. The method of claim 1, wherein the subject is a mammal.

8. The method of claim 1, wherein the subject is a human.

9. The method of claim 2, wherein the leukemia is a lymphoid leukemia or a myeloid leukemia.

10. The method of claim 1, further comprising administering the antagonist in combination with at least one additional Hh pathway antagonist.

11. The method of claim 10, wherein the additional Hh pathway antagonist is a steroidal alkaloid or derivative thereof.

12. The method of claim 11, wherein the steroidal alkaloid is cyclopamine.

13. The method of claim 1, further comprising administering the antagonist in combination with a therapeutic agent, an immunomodulatory agent, an antibody or an enzyme inhibitor.

14. The method of claim 13, wherein the therapeutic agent is selected from a group consisting of methotrexate, cisplatin/carboplatin, canbusil, dactinomicin, taxol (paclitaxel), antifolate, colchicine, demecolcine, etoposide, taxane/taxol, docetaxel, doxorubicin, anthracycline antibiotic, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate or adriamycin-14-naphthaleneacetate, irinotecan, topotecan, gemcitabine, 5-fluorouracil, leucovorin carboplatin, cisplatin, taxanes, tezacitabine, cyclophosphamide, vinca alkaloids, imatinib, anthracyclines, rituximab, trastuzumab, bevacizumab, OSI-774, and Vitaxin.

15. A method of ameliorating a hematopoietic cell malignancy in a cell having elevated Hedgehog (Hh) pathway activity in a subject as compared with a subject not having a hematopoietic cell malignancy, comprising administering to the subject an Hh pathway antagonist, thereby ameliorating the hematopoietic cell cancer in the subject, wherein the at least one Hh pathway antagonist comprises arsenic trioxide (ATO) or $NaAsO_2$.

16. The method of claim 15, wherein the hematopoietic cell malignancy is leukemia.

17. The method of claim 16, wherein the leukemia is selected from PML, AML, or CML.

18. The method of claim 17, wherein the leukemia is PML.

19. The method of claim 15, wherein the Hh pathway antagonist is an arsenical agent.

20. The method of claim 19, wherein the arsenical agent is arsenic trioxide (ATO) or $NaAsO_2$.

21. The method of claim 15, wherein the subject is a mammal.

22. The method of claim 15, wherein the subject is a human.

23. The method of claim 16, wherein the leukemia is a lymphoid leukemia or a myeloid leukemia.

24. The method of claim 15, further comprising administering the antagonist in combination with at least one additional Hh pathway antagonist.

25. The method of claim 24, further comprising administering cyclopamine.

26. The method of claim 1 or 15, wherein the antagonist antagonizes pathway activity induced by Hedgehog, SmoA1, Gli1 or Gli2 overexpression.

* * * * *